United States Patent [19]
Dobak, III et al.

[11] Patent Number: 5,827,171
[45] Date of Patent: Oct. 27, 1998

[54] INTRAVASCULAR CIRCULATORY ASSIST DEVICE

[75] Inventors: John D. Dobak, III; Kambiz Ghaerzadeh, both of San Diego, Calif.

[73] Assignee: Momentum Medical, Inc., San Jose, Calif.

[21] Appl. No.: 740,657

[22] Filed: Oct. 31, 1996

[51] Int. Cl.[6] .................................................. A61B 19/00
[52] U.S. Cl. ........................................................ 600/16
[58] Field of Search ........................... 600/16–18; 623/3; 606/192, 194, 198; 604/4–6, 65–67, 150–152, 891.1

[56] References Cited

U.S. PATENT DOCUMENTS

| | | | |
|---|---|---|---|
| 4,990,139 | 2/1991 | Jang | 606/192 X |
| 5,139,517 | 8/1992 | Corral | 623/3 |
| 5,176,619 | 1/1993 | Segalowitz | 600/18 |
| 5,213,576 | 5/1993 | Abiuso et al. | 606/192 X |
| 5,308,319 | 5/1994 | Ide et al. | 600/18 |
| 5,409,444 | 4/1995 | Kensey et al. | 600/18 |
| 5,453,076 | 9/1995 | Kiyota et al. | 600/18 |
| 5,569,184 | 10/1996 | Crocker et al. | 604/53 |

OTHER PUBLICATIONS

Abstract of U.S. Pat. No. 4,407,271 to Schiff, P.; Apparatus for Left Heart Assist; Oct. 4, 1983; patent not available.
Abstract of U.S. Pat. No. 4,522,195 to Schiff, P.; Apparatus for Left Heart Assist; Jun. 11, 1985; patent not available.
Abstract of U.S. Pat. No. 4,685,446 to Choy, D.; Method for Using a Ventricular Assist Device; Aug. 11, 1987; patent not available.
Abstract of U.S. Pat. No. 4,771,765 to Choy, D.; Heart Assist Device and Method of Use; Sep. 20, 1988; patent not available.
Abstract of U.S.Pat. No. 4,861,330 to Voss, G.; Cardiac Assist Device and Method; Aug. 29, 1989; patent not available.
Abstract of U.S. Pat. No. 4,902,273 to Choy, D.; Heart Assist Device; Feb. 20, 1990; patent not available.
Kabei, N.; *Right Ventricular Balloon Pumping*; abstract; Oct. 1985; Life Support Systems.
Moulopoulis, S.; *Intraventricular Plus Intra–aortic Balloon Pumping During Intractable Cardiac Arrest;* Nov., 1989; Circulation.
Stamatelopoulos, S.; *Left Intraventricular Balloon Pump Optimization During Intractable Cardiac Arrest;* abstract; Jul., 1996, International Journal of Artificial Organs.
Frazier, O.H.; *Clinical Use of the Hemopump;* pp. 146–152; date and place of publication unknown.
Verkerke, Bart; *The PUCA Pump: A Left Ventricular Assist Device;* pp. 365–368; 1993; Artificial Organs, vol. 17, No. 5.
Abstracts by various authors; pp. 469,551,559; 1993; Artificial Organs, vol. 17, No. 6.

*Primary Examiner*—Jeffrey R. Jastrzab
*Attorney, Agent, or Firm*—Gerald W. Spinks

[57] ABSTRACT

A circulatory assist device, having an outer balloon and an inner balloon, with a control space between the outer and inner balloons. The device is mounted on a catheter, collapsed to a sufficiently small diameter to allow insertion into the vascular system of a patient. An expansion mechanism in the device, such as a stent, can be expanded to hold the outer balloon in an expanded state, while control fluid is pumped into and evacuated from the control space to repeatedly collapse and expand the inner balloon. At least one port is formed in the inner balloon, to allow vascular fluid to enter and exit the inner balloon as the inner balloon expands and contracts. After use, the expansion mechanism is contracted to a smaller diameter to allow withdrawal from the vascular system.

53 Claims, 7 Drawing Sheets

INTRAVASCULAR CIRCULATORY ASSIST DEVICE

FEDERALLY SPONSORED RESEARCH OR DEVELOPMENT

Not Applicable

CROSS REFERENCE TO RELATED APPLICATIONS

Not Applicable

BACKGROUND OF THE INVENTION

This invention is in the field of devices used to augment or replace the pumping capacity or other flow capabilities of a vascular system, such as the cardiovascular system. In particular, the present invention is in the field of devices which can be inserted percutaneously into a vascular system to augment the pumping capabilities of the system.

There are a number of conditions which can seriously impair the ability of a vascular system to maintain its required fluid flow rate. Different vascular systems are subject to different disorders which can impair the flow of vascular fluid. In particular, in the cardiovascular system, the heart is in some circumstances unable to maintain adequate circulation of blood. Some of the conditions which can impair the ability of the heart to maintain the flow rate are myocardial infarction, physical trauma to the heart, cardiomyopathy, and infectious disease. The heart may fibrillate, or it may stop beating altogether, known as asystole, with either condition resulting in the inability to provide any flow. In addition, the performance of some surgical procedures, such as coronary artery bypass, may require that the heart be artificially arrested for the duration of the procedure.

There are also conditions in which blood flow to a single organ may be reduced. In such a case, it may be desirable to selectively perfuse the organ, applying a higher pressure than that which can be provided by the circulatory system. An example of such a condition is atherosclerotic disease of the coronary arteries. In such a condition, the lumens of one or more coronary arteries are restricted by atheroma or atherosclerotic plaque. This results in a reduction in the blood flow rate to the heart muscle distal to the restricted section of artery. This reduction in blood flow rate can result in damage to the heart muscle, or to the tissues of any other organ which is so affected, caused by a reduction of the oxygen supply to the organ. Such a condition can be alleviated, at least temporarily, by increasing the blood pressure in the artery proximal to the restriction, to increase perfusion of the organ. Theoretically, an increase in the blood pressure provided by the circulatory system can be achieved by the administration of heart stimulants, or by the administration of blood transfusions. Unfortunately, these therapies also increase the work load on the heart, thereby increasing the oxygen demand of the heart, resulting in a cancellation of the effect of the additional oxygen being supplied, where the organ being perfused is the heart. The increased demand can even exceed the additional oxygen being supplied.

Regardless of the exact nature of the reduction of flow, whether a reduction of cardiac output, a localized circulatory reduction, or a complete circulatory failure, it is desirable to be able to provide circulation of the blood with an artificial device. Such devices are commonly called circulatory assist devices. Heart failure, fibrillation, and asystole often require emergency care, because of the limited time during which remedial actions must be taken in order to be effective. In order for a circulatory assist device to be useful in the emergency care situation, the device must be quickly and easily insertable to the desired vascular location where the circulatory assistance is most effectively applied. Percutaneous application is the most advantageous procedure, because physical trauma to the patient is limited in such a procedure, and because emergency medical personnel are familiar with percutaneous insertion of various types of devices.

It is also highly desirable for a circulatory assist device to possess several other attributes. It should be capable of providing a flow rate of at least 2.5 liters per minute, while maintaining an average arterial pressure of 90 mm of Hg. The outside diameter of the device and its delivery catheter should be limited to no greater than 4 mm. This will minimize any damage to the blood vessel through which it passes. Further, this limited diameter will limit ischemia of the tissues distal of the insertion site during long periods of use. The circulatory assist device should have as few moving parts as possible, in order to minimize the chance of mechanical failure, and to limit the fabrication cost. The device should also be constructed so as to inflict as little damage as possible to blood cells. Finally, the device should be constructed so as to minimize the opportunity for coagulation within the device.

It is the object of the present invention to provide a circulatory assist device which can be mounted to a catheter for percutaneous insertion into the vascular system and for advancement to the treatment area, where increased flow is to be provided, with the diameter of the device being small enough to cause minimal trauma to the vascular system. It is a further object of the present invention to provide the circulatory assist device with a means for expanding to an operating volume, once located in the treatment area, with the operating volume being sufficiently large to provide an adequate flow rate of vascular fluid. It is a still further object of the present invention to provide the circulatory assist device with a pumping mechanism which has a minimum of moving parts, and which will cause minimal trauma to the cells of the vascular fluid.

BRIEF SUMMARY OF THE INVENTION

The present invention comprises a circulatory assist device, which, by way of example, incorporates an outer balloon mounted to a catheter, and an inner balloon mounted within the outer balloon. The inner balloon constitutes the pumping chamber. The inner balloon has at least one port through its wall, with the construction of the circulatory assist device being such that the port can be exposed to vascular fluid. The inner balloon is expanded and collapsed to cause vascular fluid, such as blood, to flow through the port into the inner balloon when it expands, and to flow out of the balloon when it collapses. This single port reciprocating type of flow can be used where the device is positioned within the left ventricle of the heart, for instance, making use of the unidirectional flow characteristics of the mitral valve and the aortic valve. Alternatively, instead of using a single port, two or more ports can be used to control the direction of flow of the fluid. For instance, the ports can be fitted with one way valves to cause the vascular fluid to enter the inner balloon through the appropriate port, and to exit the inner balloon through the appropriate port, flowing in the desired direction. Either the inlet port or the outlet port can be fitted with an external tube to draw fluid from a smaller diameter vessel, or to inject fluid into a smaller diameter vessel. This latter method could be used to provide blood flow into the feeding artery of a selected organ, such as a coronary artery.

Expansion and collapse of the inner balloon is enabled by first creating a rigid or semi-rigid housing having a substantially constant inner space within which the inner balloon can be repetitively expanded and collapsed. This constant inner space can be referred to as a control space, since it is used to provide control of the size of the inner balloon, independently of the surroundings. First, the inner and outer balloons are introduced percutaneously into the vascular system while maintained at a first, relatively small, diameter. The balloons, still in a collapsed condition, are advanced to the treatment area, such as the left ventricle of the heart. Then, the outer balloon is expanded to a selected, relatively larger, diameter, the size of which depends upon the size of the treatment area. Along with the outer balloon, an expansion mechanism is expanded to this selected larger diameter. The expansion mechanism and the outer balloon constitute the rigid or semi-rigid housing forming the control space.

The expansion mechanism is designed to maintain the larger diameter until it is reshaped to a smaller diameter for eventual withdrawal from the vascular system. The expansion mechanism can either provide the expansion force itself, or it can be expanded by fluid pressure or other forces. The expansion mechanism is located near the outer balloon; it can be positioned inside the outer balloon, or outside the outer balloon, or it can be incorporated in the wall of the outer balloon. The expansion mechanism can also be attached to the outer balloon, for instance if it is positioned outside the outer balloon. It can be an expandable stent, which is expanded by fluid pressure inside the outer balloon. This hydraulically expandable type of stent requires a protective balloon outside the outer balloon, which can be pressurized to return the stent to its smaller diameter. Alternatively, the expandable stent can be made of a thermally expandable material, such as a nickel titanium alloy. Such a thermally expandable stent can be expanded to the larger diameter by being exposed to a first temperature, such as a relatively higher temperature, and returned to the smaller diameter by being exposed to a second temperature, such as a relatively lower temperature. Exposure of the thermally expandable stent to the vascular fluid can cause it to expand, or a control fluid at the appropriate temperature can be used for this purpose. In either case, a control fluid at the desired second temperature can be used to return the thermally expandable stent to the smaller diameter.

The expansion mechanism can also take other forms. A self-expanding element can be used, such as an outwardly biased cylindrical cage or a plurality of outwardly biased flexible prongs. The self-expanding element can be retained at a smaller diameter by a retention sheath, until positioned in the treatment area. Then, the self-expanding element can be expelled from the retention sheath to allow the self-expanding element to expand to a larger diameter, thereby expanding the outer balloon along with it. The outward bias of the self-expanding element would maintain the outer balloon at the larger diameter, functioning as the rigid or semi-rigid housing, to maintain the control space within which the inner balloon operates.

Further, the expansion mechanism can take the form of a helical spring which has a larger diameter associated with a shorter length, and which has a smaller diameter associated with a longer length. The spring can be biased toward either the shorter length or the longer length. Selectively changing the length of the spring transforms its diameter accordingly. If the spring is biased toward the shorter length, it can be held under tension until positioned in the treatment area, at which time the tension can be released, allowing the spring to transform to the larger diameter. Conversely, if the spring is biased toward the longer length, it can be placed under compression once in the treatment area, transforming the spring to the shorter length and the larger diameter. In either case, reversing the process transforms the spring to the smaller diameter for withdrawal from the vascular system, once the pumping has been completed.

Regardless of the type of expansion mechanism used, a control space is created inside the outer balloon, between the outer balloon and the inner balloon. Control fluid is repeatedly pumped into, and evacuated from, this control space. When control fluid is pumped into the control space, the inner balloon collapses, expelling any vascular fluid which may be inside. When the control fluid is evacuated from the control space, the inner balloon expands, drawing in vascular fluid. Repetition of this process provides the necessary flow of vascular fluid.

The novel features of this invention, as well as the invention itself, will be best understood from the attached drawings, taken along with the following description, in which similar reference characters refer to similar parts, and in which:

DETAILED DESCRIPTION OF THE INVENTION

The present invention is a circulatory assist device which consists primarily of a pumping mechanism utilizing two coaxial balloons mounted on a catheter. The outer balloon, which is equipped with an expansion mechanism, provides a housing within which the inner balloon can expand and collapse, to take in and expel a vascular fluid. The space between the inner balloon and the outer balloon is repeatedly evacuated and then pressurized with a control fluid, to expand and collapse the inner balloon.

Figure 1:
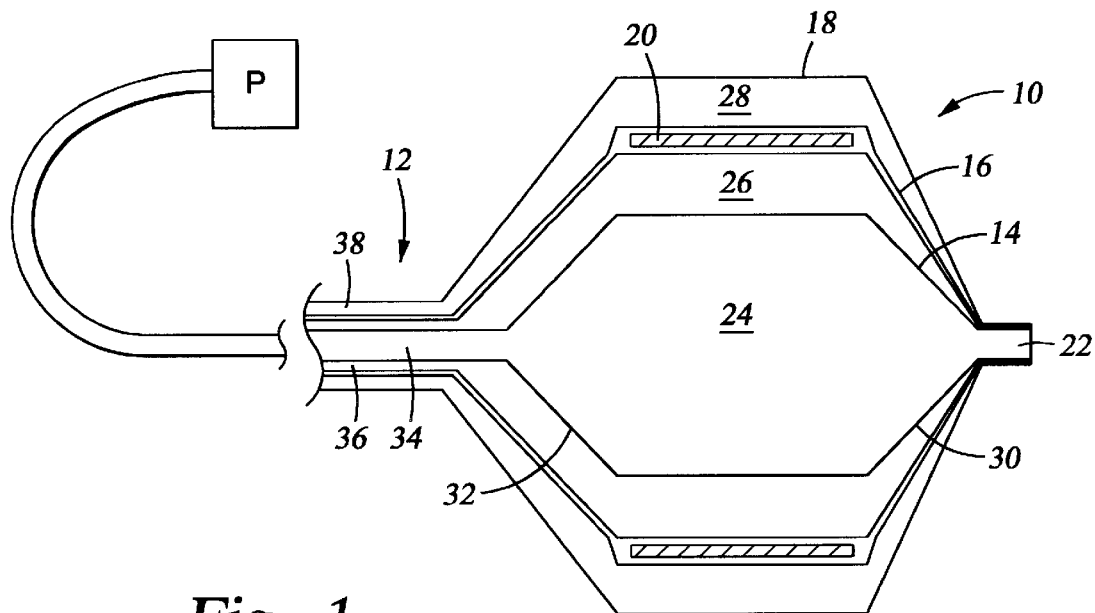
FIG. 1 is a section view of a preferred embodiment of the apparatus of the present invention.

As seen in the embodiment shown in FIG. 1, the circulatory assist device (CAD) 10 of the present invention is mounted on a catheter 12. The CAD 10 includes a flexible inner balloon 14, and a flexible outer balloon 16 surrounding the inner balloon 14. Depending upon the means by which the expansion of the CAD 10 is achieved, the CAD 10 can also be fitted with a flexible protective balloon 18, surrounding the outer balloon 16. In some embodiments, a protective balloon 18 is not required. The balloons 14, 16, 18 are made of a flexible material which can expand up to a desired size, or diameter, after which the material essentially does not expand further, even if the pressure inside the balloon is increased further. Such materials, and the processes used in their fabrication, are widely used in the manufacture of balloons for angioplasty.

An expansion mechanism, such as a substantially cylindrical expandable stent 20, is mounted in the CAD 10, near the outer balloon 16. The stent 20 can be incorporated in the wall of the outer balloon 16, or the outer balloon 16 could consist of two laminated balloons with the stent 20 captured therebetween. Alternatively, as will be illustrated below, the stent 20, or another similar expansion mechanism, could be located inside the outer balloon 16, or outside the outer balloon 16. Various other embodiments of the expansion mechanism can be used in place of the stent 20, but the stent 20 will generally be described herein, with the understanding that other embodiments could also be used. In any case, the expansion mechanism is positioned relative to, or attached to, the outer balloon 16 in such a way that the outer balloon 16 will expand with the expansion mechanism.

The stent 20 is an expandable, substantially cylindrical, lattice of elongated elements of plastic or metal. It can be similar to cardiovascular stents known in the art. The stent 20 is assembled in the CAD 10 while at a smaller diameter, substantially the diameter of the catheter 12. When the CAD 10 is positioned in the treatment area, fluid pressure can be introduced inside the stent 20 and the outer balloon 16, to expand the stent 20 to a larger diameter. When the internal pressure is released, the stent 20 will retain its larger diameter, until it is eventually compressed by the application of fluid pressure to the outer surface of the stent 20. In some other embodiments, the expansion mechanism itself provides the expanding force, such as stents made of a nickel-titanium alloy, such as nitinol, which expands upon exposure to a higher temperature. Other stents can be mechanically biased toward a larger or smaller diameter, and physically manipulated to achieve the desired diameter. In all embodiments, once expanded, the purpose of the expansion mechanism is to hold the outer balloon 16 in the expanded state.

FIG. 1 shows the CAD 10 in its expanded state, wherein the balloons 14, 16, 18 and the stent 20 are all expanded to a diameter which is relatively larger than the diameter of the catheter 12. This expanded diameter provides sufficient room for adequate pumping capacity. For use in the cardiovascular system of an adult patient, an expanded diameter of 35 mm. might be used. The balloons 14, 16, 18 and the stent are also collapsible to a relatively smaller diameter, in the range of 2.5 to 4 mm., at which the CAD 10 is essentially the same diameter as the catheter 12. This contracted diameter makes the CAD 10 small enough to be easily inserted percutaneously and advanced through the vascular system of the patient.

A port 22 for the flow of blood or other vascular fluid is formed in the distal end of the inner balloon 14, extending through the outer balloon 16 and the protective balloon 18. When the CAD 10 is positioned within a vascular system, such as the cardiovascular system, of a patient, the CAD 10 is positioned so that the port 22 is exposed to the blood in the system, at the treatment area, where circulatory assist is required. For example, depending upon the particular embodiment of the invention in use, the location of the CAD 10 could be in the left ventricle of the heart, or it could be in the aortic arch.

When the inner balloon 14 is in the expanded state, a pumping chamber 24 within the inner balloon 14 is expanded to its largest volume. The expansion of the pumping chamber 24 draws in the vascular fluid through the port 22. Subsequent collapse of the pumping chamber 24 expels the vascular fluid through the port 22. The size of the pumping chamber 24 can be designed to achieve the desired flow rate, given a selected pulse rate. For instance, if the CAD 10 is to be used in the cardiovascular system, it has been found that pulsatile flow at the frequency of the heartbeat is most beneficial. A pulse rate of 100 cycles per minute would be reasonable. In the cardiovascular system, it can be desirable to achieve a flow rate of up to 5 liters per minute. Therefore, if these parameters are assumed, the pumping chamber 24 should have a volume of 50 cc. to achieve the desired flow rate.

When the outer balloon 16 is in the expanded state, a control space 26 is created between the outer balloon 16 and the inner balloon 14. This control space 26 is repetitively evacuated and pressurized with a control fluid, to achieve the expansion and collapse of the inner balloon 14. While the outer balloon 16 is held in the expanded state by the stent 20, the total volume enclosed by the outer chamber 16 remains essentially constant, but the volume of the control space 26 decreases and increases as the inner balloon 14 expands and collapses. Pressurization of the control space 26 collapses the inner balloon 14, rather than further expanding the outer balloon 16, because the stent 20 and the outer balloon 16 have been expanded to their greatest possible diameter. Evacuation of the control space 26 expands the inner balloon 14, rather than collapsing the outer balloon 16, because the stent 20 retains its expanded diameter. This requires that the external to internal pressure differential across the outer balloon 16 during evacuation of the control space 26 be kept below the pressure differential required to compress the stent 20.

It should be noted that, in the particular embodiment discussed here, with a stent 20 which is expandable and compressible by the application of internal and external fluid pressure, the control space 26 is initially pressurized with a control fluid to expand the stent 20 and the outer balloon 16. Once this expansion of the stent 20 has been achieved, the control space 26 can then be evacuated and repressurized to achieve the pumping discussed above. When the expansion mechanism is the type which is compressed by external fluid pressure, a second control space 28 is provided between the protective balloon 18 and the outer balloon 16. The second control space 28 can be pressurized with a control fluid to compress the stent 20 and the outer balloon 16 to a smaller diameter, to allow for removal of the CAD 10 from the vascular system. Alternatively, if the thermally expandable stent 20 is used, control fluid at the desired temperature can be introduced into either of the control spaces 26, 28 to control the diameter of the stent 20 and, consequently, the outer balloon 16.

The shape of the inner balloon 14 shown here is a substantially cylindrical body, with a tapered distal end cone 30 and a tapered proximal end cone 32. The outer balloon 16 and the protective balloon 18 have similar shapes. Other shapes could also be used without departing from the spirit of the present invention.

The catheter 12 has its proximal end connected to a control fluid flow device such as a pump P. The control fluid flow device must be capable of applying a fluid pressure and drawing a vacuum. A syringe could also be used in some of the embodiments. The catheter 12 shown in FIG. 1 is a multi-lumen catheter, but some of the embodiments can be used with single-lumen catheters. A first lumen 34 can be provided in the catheter 12, to allow flow of the vascular fluid into or out of the inner balloon 14. The first lumen 34 could be used for sampling of the vascular fluid or to direct the vascular fluid from one location to another. Additional ports (not shown) could be provided proximal to the CAD 10, to allow flow of vascular fluid into or out of the first lumen 34. A second lumen 36 is provided in the catheter 12, to allow the flow of control fluid between the control fluid flow device P and the control space 26. The second lumen 36 is used to hydraulically or thermally expand the stent 20 and the outer balloon 16, and to pressurize and evacuate the control space 26 for pumping purposes. A third lumen 38 is provided in the catheter 12, to allow the flow of control fluid between the control fluid flow device P and the second control space 28. The third lumen 38 is used to thermally expand the stent 20 to create a pump housing for the inner balloon 14, or to hydraulically or thermally compress the stent 20 and the outer balloon 16 to a smaller diameter for withdrawal from the vascular system.

Figure 2:
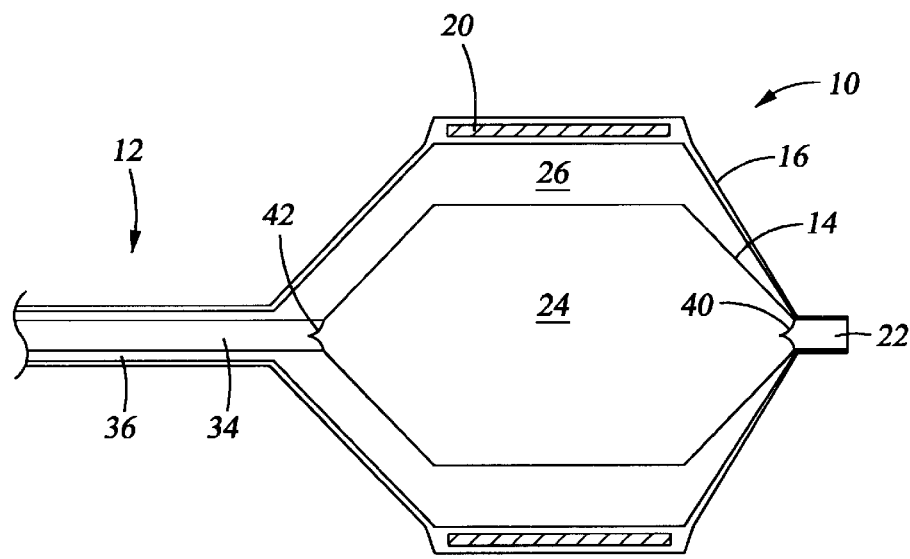
FIG. 2 is a section view of an alternate embodiment of the apparatus of the present invention, without a protective balloon.

FIG. 2 shows a second embodiment of the present invention with a few variations from the embodiment shown in FIG. 1. The stent 20 used in this embodiment is the thermally expanding stent 20 made of a material such as nitinol. A control fluid at a relatively higher temperature can be introduced into the control space 26 through the second lumen 36, to expand the stent 20. Alternatively, the vascular fluid in which the CAD 10 is immersed, such as blood, can be at a sufficiently high temperature to expand the stent 20. Compression of the stent 20 can then be achieved by introducing a control fluid at a relatively lower temperature into the control space 26. This embodiment also exhibits a one-way inlet valve 40 in the port 22, and a one-way outlet valve 42 in the first lumen 34, to control the direction of flow of the vascular fluid. The arrangement of the one-way valves 40, 42 would allow the CAD 10 to draw in blood, for instance, at the aortic arch, and direct the flow of blood to a particular artery, to perfuse a selected organ. Other arrangements of one-way valves could be used to control the direction of flow as desired for any particular application.

Figure 3:
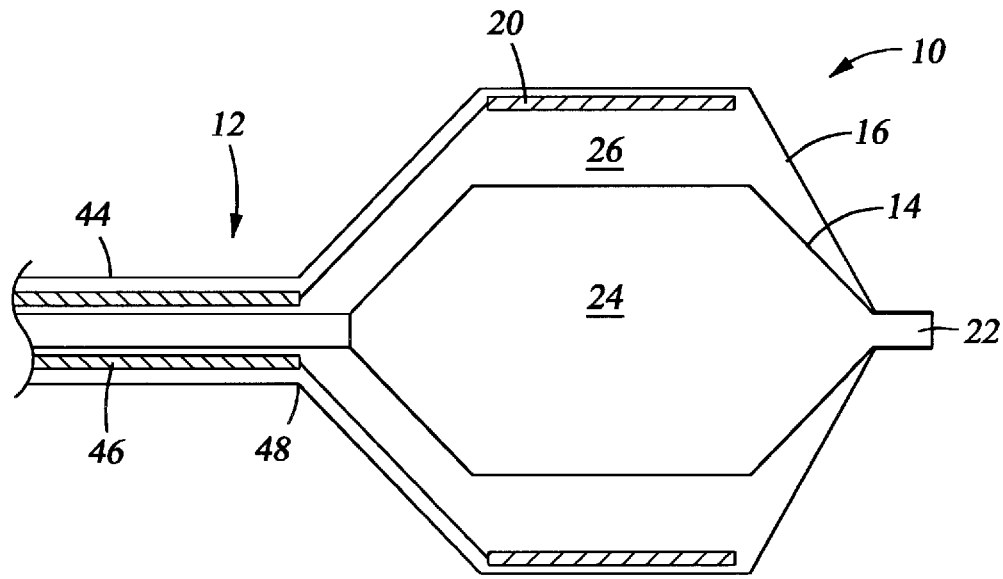
FIG. 3 is a section view of a second alternate embodiment of the apparatus of the present invention, with a first type of self-expanding element.

FIG. 3 shows an embodiment of the CAD 10 which has a self-expanding stent 20. The self-expanding stent 20 shown here is an outwardly biased cage shaped element. The stent 20 can be retained within the retention sheath 44, which is a part of the catheter 12, during insertion of the CAD 10 into the vascular system. Once the CAD 10 is positioned in the treatment area, a positioner 46 can be used to push the stent 20 beyond the distal end 48 of the retention sheath 44, allowing the stent 20 to expand to its larger diameter. Conversely, the positioner 46 can be used to pull the stent 20 back within the retention sheath 44, to reduce the diameter of the CAD 10 for withdrawal from the patient. A protective balloon 18, as shown in FIG. 1, could also be used with the self-expanding stent 20, to allow external pressurization of the stent 20 to hydraulically compress the stent 20 to its smaller diameter. Finally, the thermally expandable stent 20 could be used in the embodiment shown in FIG. 3. Ejection of the thermally expandable stent 20 from the retention sheath 44 would expose the stent 20 to the temperature of the blood, to cause the stent 20 to expand. Control fluid at a lower temperature could then be pumped into the control space 26, to return the stent 20 to its smaller diameter.

Figure 4:
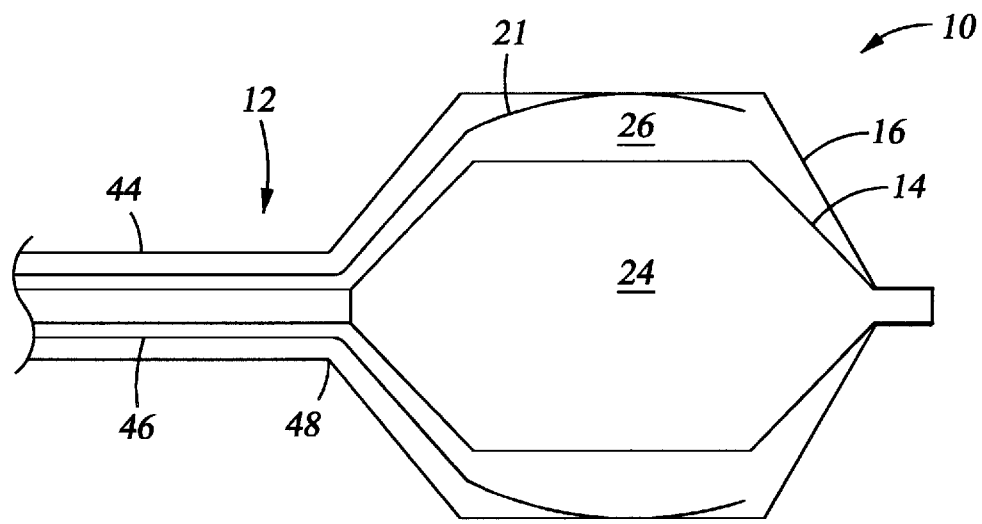
FIG. 4 is a section view of a third alternate embodiment of the apparatus of the present invention, with a second type of self-expanding element.

FIG. 4 shows a second type of the self-expanding expansion mechanism in the form of a plurality of flexible, outwardly biased prongs 21. The prongs 21 can be retained within the retention sheath 44, during insertion of the CAD 10 into the vascular system. Once the CAD 10 is positioned in the treatment area, the positioner 46 can be used to push the prongs 21 beyond the distal end 48 of the retention sheath 44, allowing the prongs 21 to expand outwardly, to stretch the outer balloon 16 to its larger diameter. Subsequently, the positioner 46 can be used to pull the prongs 21 back within the retention sheath 44, to reduce the diameter of the CAD 10 for withdrawal from the patient. A protective balloon 18, as shown in FIG. 1, could also be used with the self-expanding prongs 21, to allow pressurization of the second control space 28, to achieve hydraulic compression of the prongs 21, to return the expansion mechanism to its smaller diameter.

Figure 5:
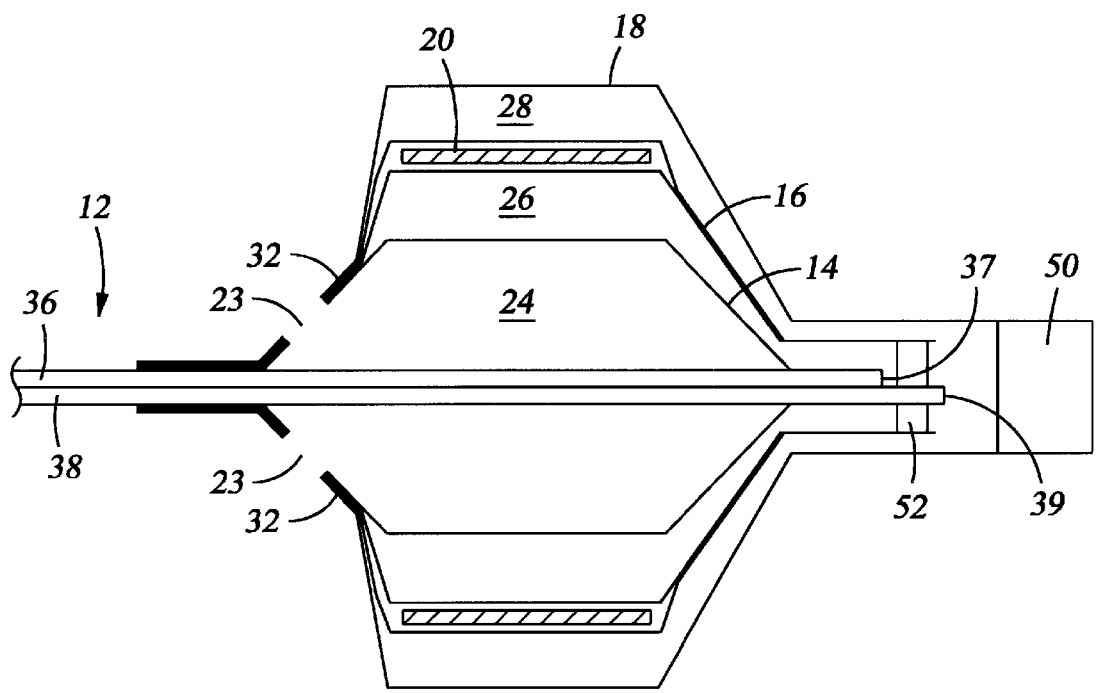
FIG. 5 is a section view of a fourth alternate embodiment of the apparatus of the present invention, with ports in the proximal cone.

FIG. 5 shows an embodiment of the invention in which the vascular fluid enters and exits the pumping chamber 24 through ports 23 located in the proximal cone 32 of the inner balloon 14. The proximal cones of the outer balloon 16 and the protective balloon 18 are bonded to the proximal cone 32 of the inner balloon 14. The catheter 12 used with this embodiment is a double-lumen tube. Pressurization and evacuation of the first control space 26 are achieved through the first control fluid lumen 36 and the inner control fluid port 37. Pressurization and evacuation of the second control space 28 are achieved through the second control fluid lumen 38 and the outer control fluid port 39. An outer plug 50 seals the distal end of the CAD 10, and an inner plug 52 seals the distal end of the outer balloon 16. This embodiment is particularly useful when it is desirable to direct the flow of vascular fluid proximally. For instance, the CAD 10 can be positioned in the left ventricle, with the ports 23 placed close to, and directed toward, the aortic valve. This would direct the flow of blood through the aortic valve, to assist the action of the ventricle. Depending upon the type of expansion mechanism used with this embodiment, such as the thermally expandable stent 20, the protective balloon 18 may be eliminated.

Figure 6:
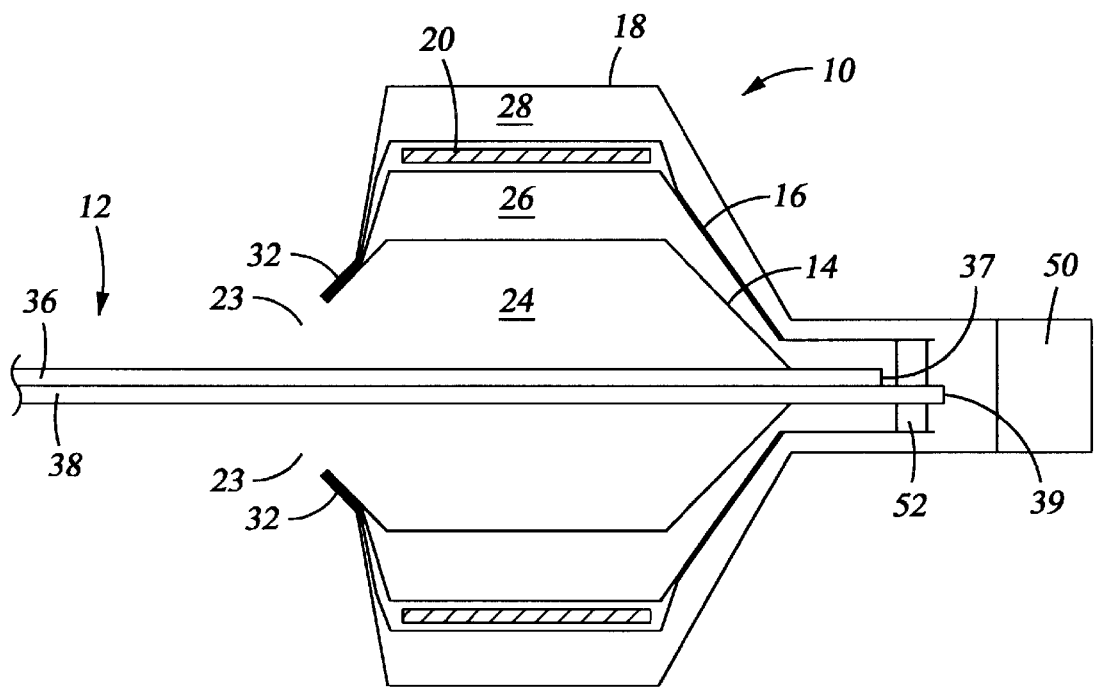
FIG. 6 is a section view of a fifth alternate embodiment of the apparatus of the present invention, with an enlarged port.

FIG. 6 shows another embodiment, which is a variation of the embodiment shown in FIG. 5. In this embodiment, the proximal cones of the balloons 14, 16, 18 are not attached to the catheter 12, and the port 23 is open all around the catheter 12. This significantly increases the cross-sectional flow area through the port 23.

Figure 7:
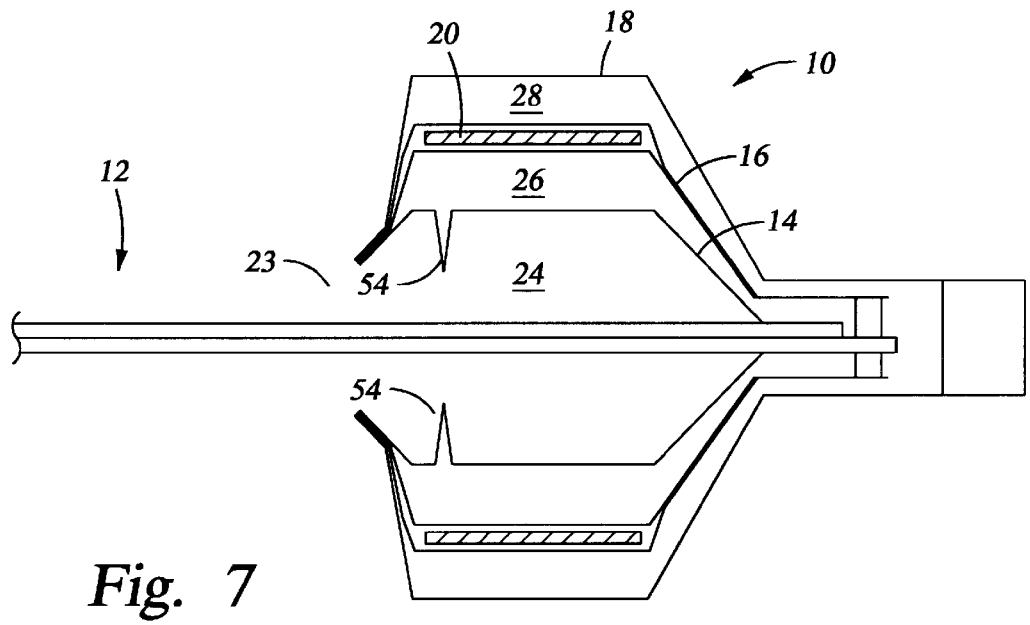
FIG. 7 is a section view of a sixth alternate embodiment of the apparatus of the present invention with a full discharge inner balloon.

In applications where it is necessary to maximize the flow of vascular fluid in each pulse, the embodiments shown in FIGS. 5 and 6 have a disadvantage in that the bonding together of the proximal cones of the balloons 14, 16, 18 can prevent the complete collapse of the inner balloon 14. This can be remedied as shown in FIG. 7, where an expansion fold 54 of material is formed in the inner balloon 14. The expansion fold 54 will fold up when the inner balloon 14 experiences expansion into the outer balloon 16, and the expansion fold 54 will distend when the inner balloon 14 collapses, allowing the inner balloon 14 to fully collapse and completely expel the vascular fluid from the pumping chamber 24.

Figure 8:
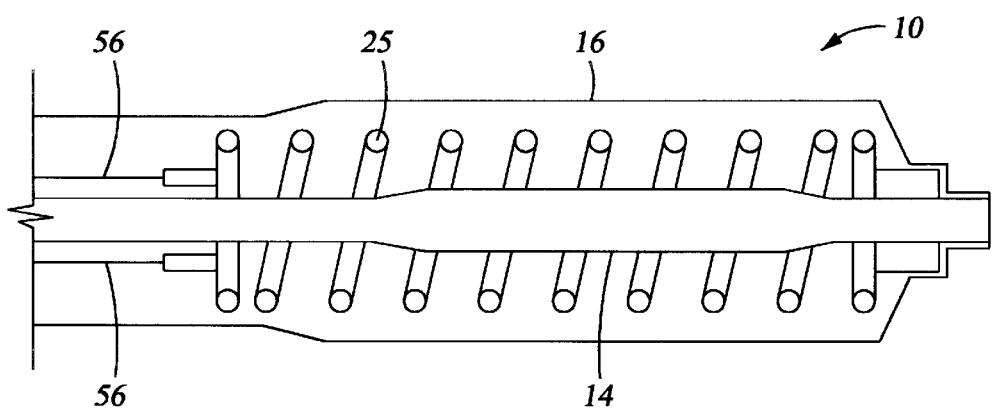
FIG. 8 is a section view of a seventh alternate embodiment of the apparatus of the present invention, with a helical spring expansion mechanism, and with the balloons in the contracted state.
Figure 9:
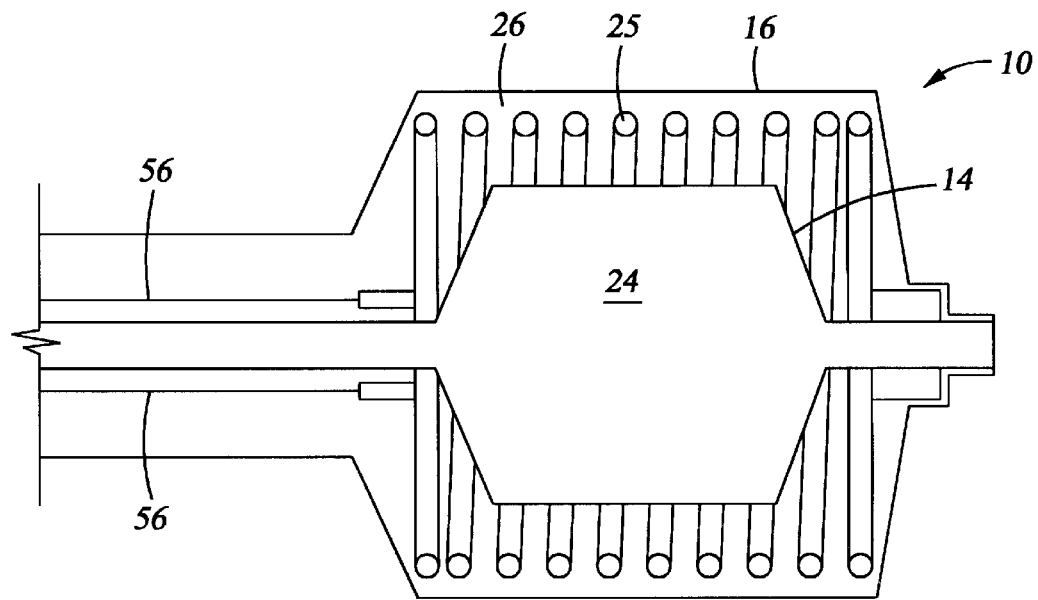
FIG. 9 is a section view of the embodiment shown in FIG. 8, in the expanded state.

FIGS. 8 and 9 show another embodiment which incorporates a self-expanding mechanism in the form of a helical spring 25. The helical spring 25 has two configurations. One configuration is shown in FIG. 8, where the length of the spring 25 is extended, and its diameter is reduced. The other configuration is shown in FIG. 9, where the length of the spring 25 is reduced, and its diameter is expanded. The distal end of the spring 25 is anchored to the distal end of the CAD 10. A spring controller 56 is attached to the proximal end of the spring 25, for transforming the spring 25 from one of these configurations to the other. Two types of spring 25 could be used.

One type of spring 25 would be biased toward the shortened configuration shown in FIG. 9, with the expanded diameter. In such a spring, it would be necessary to place the spring 25 under tension with the spring controller 56, to hold the spring 25 in the lengthened configuration, with the reduced diameter, during insertion or withdrawal of the CAD 10 through the vascular system. Then, the tension could be released to allow the spring 25 to transform to its expanded diameter to hold the outer balloon 16 in the expanded state. With this type of spring, the spring controller 56 could be either a relatively stiff member or a cable.

Another type of spring 25 would be biased toward the lengthened configuration shown in FIG. 8, with the reduced diameter. In such a spring, it would be necessary to place the spring 25 under compression with the spring controller 56, to transform the spring 25 to the shortened configuration, with the expanded diameter, to hold the outer balloon 16 in the expanded state. The spring 25 could be allowed to take its natural, lengthened, configuration during insertion or withdrawal of the CAD 10 through the vascular system. With this type of spring, the spring controller 56 must be a relatively stiff member.

Figure 10:
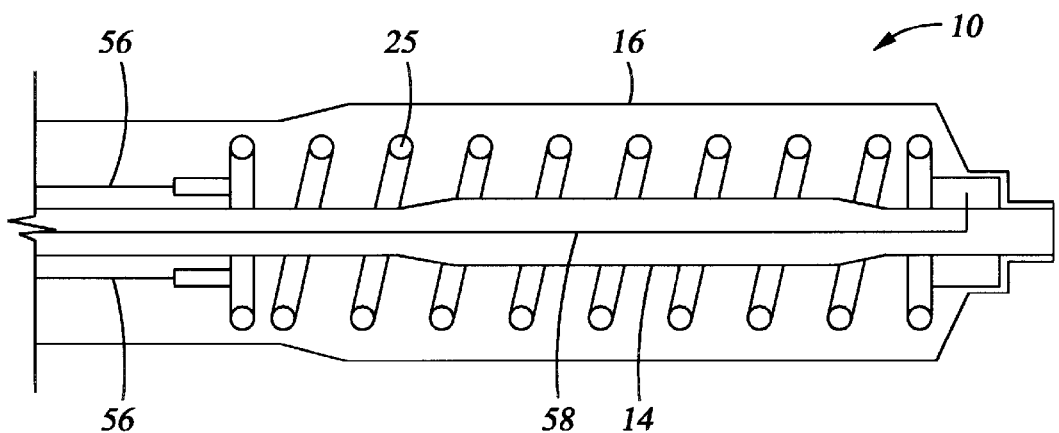
FIG. 10 is a section view of an eighth alternate embodiment of the apparatus of the present invention, with a stiffening mandrel passing through the inner balloon, and with the balloons in the contracted state.
Figure 11:
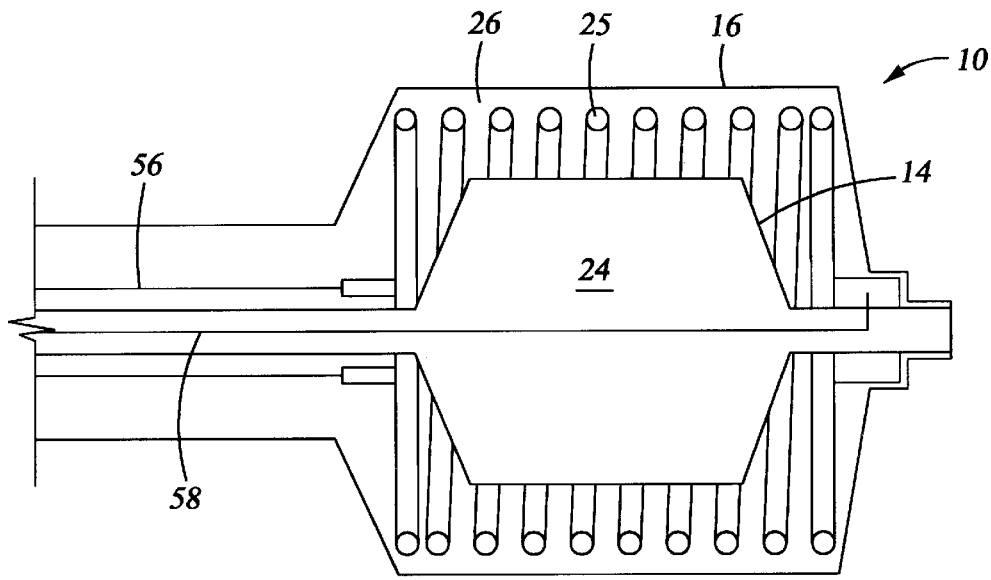
FIG. 11 is a section view of the embodiment shown in FIG. 10, in the expanded state.
Figure 12:
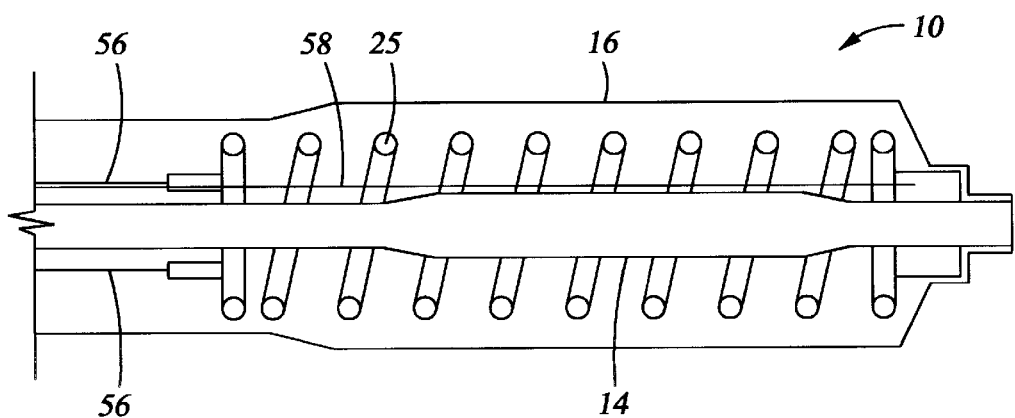
FIG. 12 is a section view of a ninth alternate embodiment of the apparatus of the present invention, with a stiffening mandrel passing outside the inner balloon, and with the balloons in the contracted state.
Figure 13:
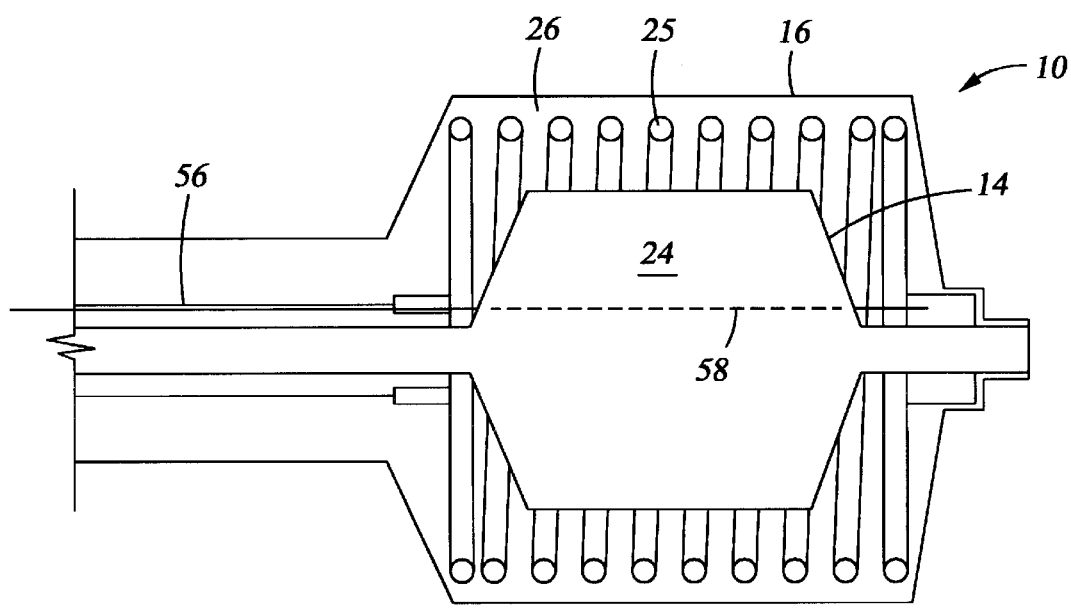
FIG. 13 is a section view of the embodiment shown in FIG. 12, in the expanded state.

When using a helical spring 25 as the expansion mechanism, it may be detrimental to rely entirely on the tensile or compressive strength of the balloons 14, 16 to resist the force in the spring 25. For instance, with the short-biased type of spring 25, the balloons 14, 16 may not have sufficient compressive strength to resist the tension placed in the spring 25 by the spring controller 56 to hold the spring in the configuration shown in FIG. 8. In such a case, the balloons 14, 16 would tend to bunch up, and the spring 25 could not be transformed to its reduced diameter for passage through the vascular system. Similarly, with the long-biased type of spring 25, the balloons 14, 16 may not have sufficient tensile strength to resist the compression placed in the spring 25 by the spring controller 56 to transform the spring 25 to the configuration shown in FIG. 9. In such a case, the balloons 14, 16 would tend to extend axially when compression of the spring 25 is attempted, and the spring 25 could not be transformed to its expanded diameter to hold the outer balloon 16 in the expanded state. The embodiments shown in FIGS. 10 through 13 can be used to alleviate this problem. FIGS. 10 and 11 show a mandrel 58 passing through the center of the inner balloon 14, and anchored to the CAD 10 at its distal end. The penetration of the mandrel 58 through the inner balloon 14 must be sealed. The mandrel 58 holds the distal ends of the balloons 14, 16 in place during application of tension or compression by the spring controller 56. If the short-biased type of spring 25 is used, the mandrel 58 must be a relatively stiff member to resist compression. If the long-biased type of spring 25 is used, the mandrel 58 can actually be very flexible, like a wire or cable. More than one mandrel 58 can be used in each CAD 10, if required for the necessary tensile or compressive strength. FIGS. 12 and 13 show a mandrel 58 passing outside the inner balloon 14, and inside the spring 25, and anchored to the CAD 10 at its distal end. This eliminates the necessity for penetrating the inner balloon 14, but the inner balloon 14 must be constructed with longitudinal folds or creases, to allow it to expand around the mandrel 58, as shown in FIG. 13.

OPERATION

The CAD 10 is arranged in its contracted, or collapsed, state, with its smallest diameter. The CAD 10 is then inserted into and through the vascular system, such as through a guide catheter well known in the art. When the CAD 10 has been advanced to the area where circulatory assist is to be provided, the expansion mechanism, such as the stent 20, is expanded along with the outer balloon 16. This expansion can be achieved hydraulically, thermally, or by manipulation of one of the forms of self-expanding elements. The expansion mechanism then holds the outer balloon 16 in the expanded state to form a pumping housing around the inner balloon 14. The first control space 26 is then evacuated to expand the inner balloon 14 and draw vascular fluid into the pumping chamber 24. Control fluid is then introduced into the first control space 26 to collapse the inner balloon 14 and expel vascular fluid from the pumping chamber 24. Upon completion of pumping, the expansion mechanism is compressed, or otherwise returned to its smaller diameter, and the CAD 10 is withdrawn from the vascular system.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A circulatory assist device, comprising:
   a flexible tubular catheter, said catheter being sized for insertion into a vascular system of a patient;
   an expandable inner balloon attached to said catheter, said inner balloon being disposable in the vascular system of the patient, with said catheter;
   an expandable outer balloon attached to said catheter, said outer balloon substantially surrounding said inner balloon;
   an expansion mechanism disposed near said outer balloon, said expansion mechanism being selectively expandable to expand said outer balloon and hold said outer balloon in said expanded state;
   a two-way control fluid flow device connected in flow communication with a control space between said inner balloon and said outer balloon, whereby selective removal of a control fluid from said control space with said control fluid flow device causes said inner balloon to expand, and whereby selective introduction of a control fluid into said control space with said control fluid flow device causes said inner balloon to collapse; and
   at least one port in said inner balloon, said port being exposable to vascular fluid, said port being capable of allowing flow of vascular fluid into said inner balloon when said inner balloon expands, and said port being capable of allowing flow of vascular fluid out of said inner balloon when said inner balloon collapses.

2. A circulatory assist device as recited in claim 1, wherein said expansion mechanism is attached to said outer balloon.

3. A circulatory assist device as recited in claim 1, wherein said expansion mechanism is disposed within said outer balloon.

4. A circulatory assist device as recited in claim 1, wherein:
   said outer balloon comprises an expandable membrane; and
   said expansion mechanism is incorporated in said expandable membrane.

5. A circulatory assist device as recited in claim 1, wherein said expansion mechanism comprises an expandable stent, said stent being expandable from a first relatively smaller diameter to a second relatively larger diameter.

6. A circulatory assist device as recited in claim 5, wherein:
   said expandable stent is expandable to said relatively larger diameter by application of internal fluid pressure; and
   said expandable stent is contractible to said relatively smaller diameter by application of external fluid pressure.

7. A circulatory assist device as recited in claim 5, wherein:
   said expandable stent is formed of a temperature actuated shape transition material, whereby:
      said expandable stent is expandable to said relatively larger diameter by exposure to a first temperature; and
      said expandable stent is contractible to said relatively smaller diameter by exposure to a second temperature.

8. A circulatory assist device as recited in claim 1, wherein said expansion mechanism comprises a self-expanding element.

9. A circulatory assist device as recited in claim 8, wherein said self-expanding element comprises a generally cylindrical cage, said cage being biased outwardly toward said relatively larger diameter.

10. A circulatory assist device as recited in claim 8, wherein said self-expanding element comprises a plurality of flexible prongs, said prongs being biased outwardly toward said relatively larger diameter.

11. A circulatory assist device as recited in claim 1, wherein:
   said expansion mechanism comprises a helical spring;
   lengthening of said spring causes said spring to have a smaller diameter; and
   shortening of said spring causes said spring to have a larger diameter.

12. A circulatory assist device as recited in claim 11, wherein said spring is biased toward said longer length and said smaller diameter, and further comprising a spring controller for compressing said spring to said shorter length, thereby causing said spring to expand to said larger diameter.

13. A circulatory assist device as recited in claim 11, wherein said spring is biased toward said shorter length and said larger diameter, and further comprising a spring controller for extending said spring to said longer length, thereby causing said spring to contract to said smaller diameter.

14. A circulatory assist device as recited in claim 1, wherein said control fluid flow device comprises a pump.

15. A circulatory assist device as recited in claim 1, wherein said control fluid flow device comprises a syringe.

16. A circulatory assist device as recited in claim 1, further comprising:
   an expandable protective balloon attached to said catheter, said protective balloon being disposed so as to substantially surround said inner and outer balloons, thereby creating a second control space between said protective balloon and said outer balloon; and
   a control fluid passageway for allowing flow of control fluid between said control fluid flow device and said second control space.

17. A circulatory assist device as recited in claim 1, wherein:
   said at least one port is located adjacent to a proximal end of said inner balloon; and
   vascular fluid both enters and exits said inner balloon near said proximal end.

18. A circulatory assist device as recited in claim 1, wherein:
   said at least one port is located adjacent to a distal end of said inner balloon; and
   vascular fluid both enters and exits said inner balloon near said distal end.

19. A circulatory assist device as recited in claim 1, wherein said at least one port comprises:
   at least one port located adjacent to a proximal end of said inner balloon; and
   at least one port located adjacent to a distal end of said inner balloon.

20. A circulatory assist device as recited in claim 19, wherein vascular fluid enters said inner balloon near one said end and exits said inner balloon near the other said end.

21. A circulatory assist device as recited in claim 1, further comprising:
   a retaining sheath for retaining said expansion mechanism in a contracted condition during passage of said catheter through a vascular system; and
   a positioner for positioning said expansion mechanism relative to said retaining sheath.

22. A circulatory assist device as recited in claim 21, wherein said positioner expels said expansion mechanism from said retaining sheath to allow said expansion mechanism to expand.

23. A circulatory assist device as recited in claim 21, wherein said positioner withdraws said expansion mechanism into said retaining sheath.

24. A circulatory assist device, comprising:
   a flexible tubular catheter, said catheter being sized for insertion into a vascular system of a patient;
   first and second lumens formed within said catheter for passage of a control fluid;
   at least one fluid flow device connected in flow communication with said first and second lumens, for moving control fluid through said lumens;
   an expandable inner balloon attached to said catheter, said inner balloon being disposable in the vascular system of the patient, with said catheter;
   an expandable outer balloon attached to said catheter, said outer balloon substantially surrounding said inner balloon;
   a first control space between said outer balloon and said inner balloon, said first control space being in fluid flow communication with said first lumen;
   an expandable protective balloon attached to said catheter, said protective balloon substantially surrounding said inner and outer balloons;
   a second control space between said protective balloon and said outer balloon, said second control space being in fluid flow communication with said second lumen;

an expandable stent disposed near said outer balloon, said expandable stent being selectively expandable from a smaller diameter to a larger diameter by application of control fluid pressure to said first control space, said stent being capable of retaining said larger diameter upon release of said fluid pressure in said first control space, to hold said outer balloon at said larger diameter, said stent being selectively contractible from said larger diameter to said smaller diameter by application of control fluid pressure to said second control space; and at least one port in said inner balloon, said at least one port being exposable to vascular fluid, for allowing flow of vascular fluid into said inner balloon when said inner balloon expands, and for allowing flow of vascular fluid out of said inner balloon when said inner balloon collapses;

wherein, after expansion of said stent, said fluid flow device is capable of selectively evacuating control fluid from said first control space to cause said inner balloon to expand, and said fluid flow device is capable of selectively introducing control fluid into said first control space to cause said inner balloon to collapse.

25. A circulatory assist device as recited in claim 24, wherein said expandable stent is attached to said outer balloon.

26. A circulatory assist device as recited in claim 24, wherein said expandable stent is disposed within said outer balloon.

27. A circulatory assist device as recited in claim 24, wherein:
said outer balloon comprises an expandable membrane; and
said expandable stent is incorporated in said expandable membrane.

28. A circulatory assist device as recited in claim 24, wherein said fluid flow device comprises a pump.

29. A circulatory assist device as recited in claim 24, wherein said fluid flow device comprises a syringe.

30. A circulatory assist device, comprising:
a flexible tubular catheter, said catheter being sized for insertion into a vascular system of a patient;
a lumen formed within said catheter for passage of a control fluid;
a fluid flow device connected in flow communication with said lumen, for moving control fluid through said lumen;
an expandable inner balloon attached to said catheter, said inner balloon being disposable in the vascular system of the patient, with said catheter;
an expandable outer balloon attached to said catheter, said outer balloon substantially surrounding said inner balloon;
a control space between said outer balloon and said inner balloon, said control space being in fluid flow communication with said lumen;
an expandable stent disposed near said outer balloon, said expandable stent being formed of a temperature actuated shape transition material, said expandable stent thereby being selectively expandable from a smaller diameter to a larger diameter by exposure to a first temperature, to hold said outer balloon at said larger diameter, said stent thereby being selectively contractible from said larger diameter to said smaller diameter by exposure to a second temperature; and
at least one port in said inner balloon, said at least one port being exposable to vascular fluid, for allowing flow of vascular fluid into said inner balloon when said inner balloon expands, and for allowing flow of vascular fluid out of said inner balloon when said inner balloon collapses;

wherein, after expansion of said stent, selectively evacuating control fluid from said control space with said fluid flow device causes said inner balloon to expand, and selectively introducing control fluid into said control space with said fluid flow device causes said inner balloon to collapse.

31. A circulatory assist device as recited in claim 30, further comprising means for providing control fluid at said first temperature and said second temperature, said control fluid causing said stent to expand when introduced into said control space at said first temperature, and said control fluid causing said stent to contract when introduced into said control space at said second temperature.

32. A circulatory assist device, comprising:
a flexible tubular catheter, said catheter being sized for insertion into a vascular system of a patient;
a lumen formed within said catheter for passage of a control fluid;
a fluid flow device connected in flow communication with said lumen, for moving control fluid through said lumen;
an expandable inner balloon attached to said catheter, said inner balloon being disposable in the vascular system of the patient, with said catheter;
an expandable outer balloon attached to said catheter, said outer balloon substantially surrounding said inner balloon;
a control space between said outer balloon and said inner balloon, said control space being in fluid flow communication with said lumen;
a self-expanding mechanism retainable in a retention cavity near said outer balloon, said self-expanding mechanism being selectively expandable from a smaller diameter to a larger diameter by release from said retention cavity, to hold said outer balloon at said larger diameter, said self-expanding mechanism being selectively contractible from said larger diameter to said smaller diameter by withdrawal into said retention cavity; and
at least one port in said inner balloon, said at least one port being exposable to vascular fluid, for allowing flow of vascular fluid into said inner balloon when said inner balloon expands, and for allowing flow of vascular fluid out of said inner balloon when said inner balloon collapses; wherein, after expansion of said self-expanding mechanism, said fluid flow device is capable of selectively evacuating control fluid from said control space to cause said inner balloon to expand, and said fluid flow device is capable of selectively introducing control fluid into said control space to cause said inner balloon to collapse.

33. A circulatory assist device as recited in claim 32, wherein said self-expanding element comprises a generally cylindrical cage, said cage being biased outwardly toward said relatively larger diameter.

34. A circulatory assist device as recited in claim 32, wherein said self-expanding element comprises a plurality of flexible prongs, said prongs being biased outwardly toward said relatively larger diameter.

35. A circulatory assist device, comprising:
a flexible tubular catheter, said catheter being sized for insertion into a vascular system of a patient;

a lumen formed within said catheter for passage of a control fluid;

a fluid flow device connected in flow communication with said lumen, for moving control fluid through said lumen;

an expandable inner balloon attached to said catheter, said inner balloon being disposable in the vascular system of the patient, with said catheter;

an expandable outer balloon attached to said catheter, said outer balloon substantially surrounding said inner balloon;

a control space between said outer balloon and said inner balloon, said control space being in fluid flow communication with said lumen;

a helical spring near said outer balloon, said spring having a smaller diameter at a relatively longer length, and said spring having a larger diameter at a relatively shorter length, to hold said outer balloon at said larger diameter; and at least one port in said inner balloon, said at least one port being exposable to vascular fluid, for allowing flow of vascular fluid into said inner balloon when said inner balloon expands, and for allowing flow of vascular fluid out of said inner balloon when said inner balloon collapses;

wherein, after transformation of said helical spring to said larger diameter, selectively evacuating control fluid from said control space with said fluid flow device causes said inner balloon to expand, and selectively introducing control fluid into said control space with said fluid flow device causes said inner balloon to collapse.

36. A circulatory assist device as recited in claim 35, wherein said spring is biased toward said longer length and said smaller diameter, and further comprising a spring controller for compressing said spring to said shorter length, thereby causing said spring to transform to said larger diameter.

37. A circulatory assist device as recited in claim 35, wherein said spring is biased toward said shorter length and said larger diameter, and further comprising a spring controller for extending said spring to said longer length, thereby causing said spring to transform to said smaller diameter.

38. A method of assisting circulation of a vascular fluid, comprising:

providing a catheter mounted circulation device having an inner balloon and an outer balloon, with a control space between said inner and outer balloons, said circulation device also having an expansion mechanism for mechanically holding said outer balloon in an expanded state, said circulation device having at least one port leading into the interior of said inner balloon;

inserting said circulation device through a vascular system of a patient, to a desired location where said at least one port of said inner balloon is exposed to vascular fluid;

expanding said outer balloon and said expansion mechanism;

holding said outer balloon in said expanded state with said expansion mechanism;

introducing a control fluid into said control space to collapse said inner balloon, thereby expelling vascular fluid from said at least one port; and evacuating control fluid from said control space to expand said inner balloon, thereby drawing vascular fluid into said interior of said inner balloon.

39. A method of assisting circulation of a vascular fluid, as recited in claim 38, further comprising:

applying control fluid pressure into the interior of said outer balloon, through said catheter, to hydraulically expand said outer balloon and said expansion mechanism; and releasing said control fluid pressure in said interior of said outer balloon, leaving said outer balloon held in said expanded state by said expansion mechanism.

40. A method of assisting circulation of a vascular fluid, as recited in claim 38, further comprising:

applying a fluid at a first temperature to thermally expand said expansion mechanism; and applying a fluid at a second temperature to thermally contract said expansion mechanism for withdrawal from the vascular system.

41. A method of assisting circulation of a vascular fluid, as recited in claim 40, wherein:

said fluid at said first temperature is control fluid; and said fluid at said second temperature is control fluid.

42. A method of assisting circulation of a vascular fluid, as recited in claim 40, wherein:

said fluid at said first temperature is vascular fluid; and said fluid at said second temperature is control fluid.

43. A method of assisting circulation of a vascular fluid, as recited in claim 38, further comprising:

providing a protective balloon surrounding said outer balloon, creating a second control space between said outer balloon and said protective balloon; and introducing a control fluid into said second control space to control the diameter of said expansion mechanism.

44. A method of assisting circulation of a vascular fluid, as recited in claim 43, wherein said step of controlling the diameter of said expansion mechanism comprises:

applying control fluid at a first temperature to expand said expansion mechanism; and applying control fluid at a second temperature to contract said expansion mechanism.

45. A method of assisting circulation of a vascular fluid, as recited in claim 43, wherein said step of controlling the diameter of said expansion mechanism comprises pressurizing said second control space with control fluid to compress said expansion mechanism to said smaller diameter.

46. A method of assisting circulation of a vascular fluid, as recited in claim 38, wherein said expansion mechanism comprises a self-expanding element, and said method further comprises:

releasing said self-expanding element from a retention cavity, thereby allowing said self-expanding element to expand and hold said outer balloon in said expanded state; and withdrawing said self-expanding element into said retention cavity, thereby contracting said self-expanding element to a contracted state for withdrawal of said catheter from the vascular system.

47. A method of assisting circulation of a vascular fluid, as recited in claim 38, wherein said expansion mechanism comprises a spring and a spring controller, and said method further comprises:

shortening the length of said spring with said spring controller, thereby transforming said spring to a larger diameter, to expand and hold said outer balloon in said expanded state; and extending the length of said spring with said spring controller, thereby transforming said spring to a smaller diameter, for withdrawal of said catheter from the vascular system.

48. A method of assisting circulation of a vascular fluid, as recited in claim 47, wherein said spring is biased toward said shortened length, and said expansion of the diameter of said spring comprises releasing said spring from tension with said spring controller.

49. A method of assisting circulation of a vascular fluid, as recited in claim 47, wherein said spring is biased toward said extended length, and said expansion of the diameter of said spring comprises applying compression force to said spring with said spring controller.

50. A circulatory assist device, comprising:

a flexible tubular catheter, said catheter being sized for insertion into a vascular system of a patient;

a selectively expandable inner membrane attached to said catheter, said inner membrane being disposable in the vascular system of the patient, with said catheter;

a selectively expandable outer membrane attached to said catheter, said outer membrane substantially surrounding said inner membrane;

a retention means for retaining said outer membrane in an expanded state;

a two-way control fluid flow device connected in flow communication with a control space adjacent said inner membrane, whereby selective introduction of a control fluid into, and removal of a control fluid from, said control space, with said control fluid flow device, causes said inner membrane to expand and collapse;

a pumping chamber within at least said outer membrane; and at least one port into said pumping chamber, said port being exposable to vascular fluid, said port being capable of allowing flow of vascular fluid into, and allowing flow of vascular fluid out of, said pumping chamber, when said inner membrane expands and collapses.

51. A circulatory assist device, comprising:

a flexible tubular catheter, said catheter being sized for insertion into a vascular system of a patient;

a selectively expandable inner membrane attached to said catheter, said inner membrane being disposable in the vascular system of the patient, with said catheter;

a selectively expandable outer membrane attached to said catheter, said outer membrane substantially surrounding said inner membrane:

a retention means for retaining said outer membrane in an expanded state;

a two-way control fluid flow device connected in flow communication with a control space adjacent said inner membrane, whereby selective introduction of a control fluid into, and removal of a control fluid from, said control space, with said control fluid flow device, causes said inner membrane to expand and collapse;

a pumping chamber within at least said outer membrane; and at least one port into said pumping chamber, said port being exposable to vascular fluid, said port being capable of allowing flow of vascular fluid into, and allowing flow of vascular fluid out of, said pumping chamber, when said inner membrane expands and collapses;

wherein:

said pumping chamber is within said inner membrane;

said control space is between said inner membrane and said outer membrane, causing said inner membrane to collapse upon introduction of said control fluid into said control space, and causing said inner membrane to expand upon removal of said control fluid from said control space; and said port is in said inner membrane, to allow flow of vascular fluid into and out of said pumping chamber within said inner membrane, as said inner membrane expands and collapses.

52. A method of assisting circulation of a vascular fluid, comprising:

providing a catheter mounted circulation device having an inner membrane and an outer membrane, with a control space adjacent said inner membrane, said outer membrane also being mechanically fixable in an expanded state, said circulation device having at least one vascular fluid flow port;

inserting said circulation device through a vascular system of a patient, to a desired location where said at least one vascular fluid flow port is exposed to vascular fluid;

expanding said outer membrane;

holding said outer membrane in said expanded state;

alternatingly introducing a control fluid into said control space and evacuating control fluid from said control space to alternatingly expand and collapse said inner membrane, thereby drawing vascular fluid into, and expelling vascular fluid from, said circulation device.

53. A method of assisting circulation of a vascular fluid as recited in claim 52, wherein:

said control space is between said inner membrane and said outer membrane;

said at least one vascular fluid flow port is in said inner membrane;

said introduction of said control fluid into said control space collapses said inner membrane, thereby expelling said vascular fluid from said inner membrane; and said evacution of said control fluid from said control space expands said inner membrane, thereby drawing said vascular fluid into said inner membrane.

* * * * *